United States Patent
Pham et al.

(10) Patent No.: US 12,161,836 B2
(45) Date of Patent: Dec. 10, 2024

(54) FLEXIBLE CANNULA AND PROCESS

(71) Applicant: Medtronic MiniMed, Inc., Northridge, CA (US)

(72) Inventors: An Thien Pham, Rosemead, CA (US); Matthew William Yavorsky, Granada Hills, CA (US); Amith Wijesuriya, Los Angeles, CA (US); Yevgeniy Levin, West Hills, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 44 days.

(21) Appl. No.: 16/436,496

(22) Filed: Jun. 10, 2019

(65) Prior Publication Data

US 2020/0384187 A1   Dec. 10, 2020

(51) Int. Cl.
| | |
|---|---|
| *A61M 25/00* | (2006.01) |
| *A61B 17/34* | (2006.01) |
| *A61M 5/142* | (2006.01) |
| *A61M 5/158* | (2006.01) |
| *A61M 39/08* | (2006.01) |

(52) U.S. Cl.
CPC ......... *A61M 5/142* (2013.01); *A61B 17/3421* (2013.01); *A61M 5/158* (2013.01); *A61M 39/08* (2013.01); *A61B 17/3415* (2013.01); *A61M 2005/1585* (2013.01); *A61M 2005/1587* (2013.01); *A61M 2025/0042* (2013.01); *A61M 25/0043* (2013.01); *A61M 25/0054* (2013.01)

(58) Field of Classification Search
CPC ...... A61M 5/142; A61M 5/158; A61M 39/08; A61M 25/0043; A61M 2005/1585; A61M 2005/1587; A61M 25/0054; A61M 25/0021; A61M 25/0013; A61M 2025/0024; A61B 17/3421; A61B 17/3415

See application file for complete search history.

(56) References Cited

U.S. PATENT DOCUMENTS

| | | | | |
|---|---|---|---|---|
| 5,409,469 | A * | 4/1995 | Schaerf | A61M 25/0662 604/524 |
| 5,681,296 | A * | 10/1997 | Ishida | B29C 41/386 600/585 |
| 10,821,225 | B2 * | 11/2020 | Yavorsky | A61M 5/158 |
| 2007/0224309 | A1 * | 9/2007 | Mejlhede | B29C 45/261 604/27 |
| 2011/0313357 | A1 * | 12/2011 | Skutnik | A61M 25/007 264/254 |

(Continued)

FOREIGN PATENT DOCUMENTS

DE   102008030966 A1 *   1/2010  ........ A61M 25/0023

*Primary Examiner* — Phillip A Gray
*Assistant Examiner* — Anne E Goldberg-Richmeier
(74) *Attorney, Agent, or Firm* — Foley & Lardner LLP (57) ABSTRACT

A flexible tubing for a cannula has a hollow tubing body having a length dimension from a first end to a second end, and an outer diameter of no more than 0.9 mm. The tubing body has a section of enhanced flexibility of a greater flexibility than one or more other sections of the tubing body. The section of enhanced flexibility is spaced from the first end of the tubing body by a distance D, where D is within a range of 3.0 mm to 5.0 mm for a flexible tubing having a length of about 9.0 mm, and where D is within a range of 1.0 mm to 2.9 mm for a flexible tubing having a length of about 6.0 mm.

20 Claims, 3 Drawing Sheets

(56) References Cited

U.S. PATENT DOCUMENTS

| | | | |
|---|---|---|---|
| 2014/0350515 A1* | 11/2014 | Abbasi | A61M 27/00 |
| | | | 604/506 |
| 2018/0015254 A1* | 1/2018 | Cragg | A61M 25/0108 |
| 2018/0207355 A1* | 7/2018 | Yavorsky | A61M 39/08 |
| 2018/0207356 A1* | 7/2018 | Joseph | A61M 39/0247 |
| 2018/0318549 A1 | 11/2018 | Chiu et al. | |
| 2018/0318550 A1 | 11/2018 | Chiu et al. | |
| 2020/0206458 A1* | 7/2020 | Mullins | A61M 25/0054 |
| 2021/0268179 A1* | 9/2021 | Schøndorff | A61B 17/3417 |

* cited by examiner

FLEXIBLE CANNULA AND PROCESS

BACKGROUND

Various types of modern medical devices include or employ flexible tubing for conveying fluid media through a flow passage in the tubing. Such flexible tubing may be employed for conveying fluid media to or from a patient, a sensor, a pump, an insertion set or other medical device, a reservoir or fluid container, an implanted or partially implanted device, or the like. Such flexible tubing may be included in a sensor, a pump, in insertion set or other medical device. In addition, flexible tubing may be employed for forming a cannula configured to be inserted into or partially into a patient, for example, through the patient's skin.

Certain diseases or conditions may be treated, according to modern medical techniques, by delivering a medication or other substance to the body of a user, through a cannula or other tubing, either in a continuous manner or at particular times or time intervals within an overall time period. For example, diabetes is commonly treated by delivering defined amounts of insulin to the user at appropriate times. Some common modes of providing insulin therapy to a user include delivery of insulin through manually operated syringes and insulin pens. Other modern systems employ programmable fluid infusion devices (e.g., insulin pumps) to deliver controlled amounts of insulin to a user. In certain instances, these fluid infusion devices employ an insertion set, such as an infusion set, to be coupled to the body of a user for the delivery of the insulin. Typically, the infusion set includes a portion of a cannula that can be, for example, inserted under the skin of the user to deliver controlled amounts of infusion media (e.g., insulin) to the user. Various examples of infusions sets that include a flexible tubing cannula are described in U.S. Patent Application Publication No. 2018/0318550 (application Ser. No. 15/973,471). Example flexible tubings as described herein may be employed with or included in those or other suitable infusion set devices. Example flexible tubings as described herein may be employed with other medical devices and systems for conveying fluid media to or from a patient, a sensor, a pump, an insertion set or other device or system.

For example, a flexible tubing cannula or an insertion set with a cannula may be configured or employed as a sensor set, to couple a sensor to a body of the user. For example, a sensor set may be configured to monitor glucose levels with a sensor set, to measure glucose levels in blood or interstitial fluid.

In certain contexts and applications of use, such as, but not limited to contexts in which the flexible tubing forms a cannula for insertion through a patient's skin, it can be desirable for the size of the outer diameter of the flexible tubing to be relatively small (or minimized) for patient comfort, while still providing sufficient fluid flow capacity through the tubing. In addition, it may be desirable for the tubing to have a degree of flexibility, to allow the tubing to flex or move with the patient's skin, but also withstand kinking or buckling when bent or curved. A thin, flexible tubing can improve patient comfort during insertion and use of the cannula. In certain contexts and applications of use, the cannula may be configured to be inserted through a patient's skin and extend a distance, subcutaneously within the patient. In such contexts, the cannula may abut against relatively dense tissue (such as, but not limited to muscle tissue), which may cause the flexible cannula to bend.

Examples tubing configurations described herein can provide a relatively thin outer diameter and have one or more sections of enhanced flexibility that control or define one or more bending location (or primary bending locations) along the length of the tubing, and inhibit buckling or kinking at the bending location. In certain examples, the one or more sections of enhanced flexibility is provided at a defined distance from an end of the cannula, to control or define the bending location relative to that end of the cannula. In certain examples, the defined distance is based, at least in part, on the length dimension of the flexible tubing cannula (or the body weight of the patient).

SUMMARY

One or more examples and aspects described herein relate to a flexible tubing for a cannula, where the flexible tubing has a hollow tubing body having a length dimension extending from a first end to a second end and an outer diameter of no more than 0.9 mm. The tubing body has at least one section of enhanced flexibility located between the first and the second end. The at least one section of enhanced flexibility has a greater flexibility than one or more other sections of the tubing body.

In a further example of that flexible tubing, the at least one section of enhanced flexibility is spaced from the first end of the tubing body by a distance D, where D is within a range of 3.0 mm to 5.0 mm.

In a further example of that flexible tubing, the length dimension of the tubing body is no more than about 6.0 mm.

In a further example of that flexible tubing, the at least one section of enhanced flexibility is located at a distance D from the first end of the tubing body, where D within a range of 1.0 mm to 3.0 mm.

In a further example of that flexible tubing, the length dimension of the tubing body is greater than 6.0 mm, but no more than about 9.0 mm.

In a further example of that flexible tubing, the tubing body has a tubing wall and wherein the at least one section of enhanced flexibility comprises one or more folds or convolutions in the tubing wall.

In a further example of that flexible tubing, the tubing body defines a circumference and wherein the one or more folds or convolutions extend around the entire circumference of the tubing body.

In a further example of the flexible tubing, the tubing body defines a circumference and wherein the one or more folds or convolutions extend around part of, but not the entire circumference of the tubing body.

In a further example of the flexible tubing, the one or more folds or convolutions form a spiral or helical shape on the tubing wall.

In a further example of the flexible tubing, the tubing wall has an inner surface and an outer surface and wherein the at least one section of enhanced flexibility is provided on the outer surface of the tubing wall, but not on the inner surface of the tubing wall.

In a further example of the flexible tubing, the tubing wall has an inner surface and an outer surface and wherein the at least one section of enhanced flexibility is provided on an inner surface of the tubing wall, but not on an outer surface of the tubing wall.

In a further example of the flexible tubing, the tubing body has a tubing wall and wherein the at least one section of enhanced flexibility comprises a plurality of folds or convolutions in the tubing wall.

In a further example of that flexible tubing, the plurality of folds or convolutions are provided at a pitch within the range of about 0.125 mm and about 1.0 mm.

In a further example of the flexible tubing, the tubing body has a tubing wall and wherein the at least one section of enhanced flexibility comprises no more than one fold or convolution in the tubing wall.

In a further example of that flexible tubing, the fold or convolution extends around the entire circumference of the tubing body.

In a further example of that flexible tubing, the fold or convolution extends around part of, but not the entire circumference of the tubing body.

In a further example of that flexible tubing, the fold or convolution forms a spiral or helical shape on the tubing wall.

In a further example of the flexible tubing, the tubing body has a tubing wall having an inner surface and an outer surface, and wherein a plurality of bumps, bubbles or protrusions are provided on the inner surface of the tubing wall.

An example of a method of making a flexible tubing for a cannula includes forming a hollow tubing body having a length dimension extending from a first end to a second end and an outer diameter of no more than 0.9 mm, and providing the tubing body with at least one section of enhanced flexibility located between the first and the second end. The at least one section of enhanced flexibility has a greater flexibility than one or more other sections of the tubing body.

In a further example of that method the at least one section of enhanced flexibility is spaced from the first end of the tubing body by a distance D, where D is within a range of 1.0 mm to 2.9 mm and the length dimension of the tubing body is no more than about 6.0 mm, or where D is within a range of 3.0 mm to 5.0 mm and the length dimension of the tubing body is greater than 6 mm and no more than about 9.0 mm.

BRIEF DESCRIPTION OF THE DRAWINGS

The above and other aspects and features of the present invention will become more apparent to those skilled in the art from the following detailed description of the example embodiments with reference to the accompanying drawings, in which.

DETAILED DESCRIPTION

Hereinafter, example embodiments will be described in more detail with reference to the accompanying drawings. The present invention, however, may be embodied in various different forms, and should not be construed as being limited to only the illustrated embodiments herein. Rather, these embodiments are provided as examples so that this disclosure will be thorough and complete, and will fully convey the aspects and features of the present invention to those skilled in the art. Accordingly, processes, elements, and techniques that are not necessary to those having ordinary skill in the art for a complete understanding of the aspects and features of the present invention may not be described. Unless otherwise noted, like reference numerals denote like elements throughout the attached drawings and the written description, and thus, descriptions thereof may not be repeated. Further, features or aspects within each example embodiment should typically be considered as available for other similar features or aspects in other example embodiments.

Certain terminology may be used in the following description for the purpose of reference only, and thus are not intended to be limiting. For example, terms such as "top", "bottom", "upper", "lower", "above", and "below" could be used to refer to directions in the drawings to which reference is made. Terms such as "front", "back", "rear", "side", "outboard", and "inboard" could be used to describe the orientation and/or location of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second", and other such numerical terms referring to structures do not imply a sequence or order unless clearly indicated by the context.

It will be understood that when an element or feature is referred to as being "on," "connected to," or "coupled to" another element or layer, it can be directly on, connected to, or coupled to the other element or feature, or one or more intervening elements or features may be present. In addition, it will also be understood that when an element or features is referred to as being "between" two elements or features, it can be the only element or feature between the two elements or features, or one or more intervening elements or features may also be present.

The terminology used herein is for the purpose of describing particular embodiments and is not intended to be limiting of the present invention. As used herein, the singular forms "a" and "an" are intended to include the plural forms as well, unless the context clearly indicates otherwise. It will be further understood that the terms "comprises," "comprising," "includes," and "including," "has, " "have, " and "having," when used in this specification, specify the presence of the stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list.

As used herein, the term "substantially," "about," and similar terms are used as terms of approximation and not as terms of degree, and are intended to account for the inherent variations in measured or calculated values that would be recognized by those of ordinary skill in the art. Further, the use of "may" when describing embodiments of the present invention refers to "one or more embodiments of the present invention." As used herein, the terms "use," "using," and "used" may be considered synonymous with the terms "utilize," "utilizing," and "utilized," respectively.

Unless otherwise defined, all terms (including technical and scientific terms) used herein have the same meaning as commonly understood by one of ordinary skill in the art to which the present invention belongs. It will be further understood that terms, such as those defined in commonly used dictionaries, should be interpreted as having a meaning that is consistent with their meaning in the context of the relevant art and/or the present specification, and should not be interpreted in an idealized or overly formal sense, unless expressly so defined herein.

Various types of modern medical devices and cannulas include or employ hollow, flexible tubing for conveying fluid media. Example embodiments relate to hollow flexible tubing for conveying fluid media, and further example embodiments relate to medical devices and systems that include such flexible tubing.

In particular examples, the flexible tubing may be relatively flexible along its length, but is also configured to have a relatively high degree of flexibility (or enhanced flexibility) in one or more selected sections of the length of the tubing, to allow bending at a controlled location or in a controlled manner (or both). In other examples, the flexible tubing may be relatively rigid along sections of its length but have one or more sections of enhanced flexibility, to allow bending only within the one or more sections of enhanced flexibility. In particular examples, the flexible tubing is configured to provide a relatively high resistance to kinking or buckling, when bending at the one or more sections of enhanced flexibility.

Figure 1:
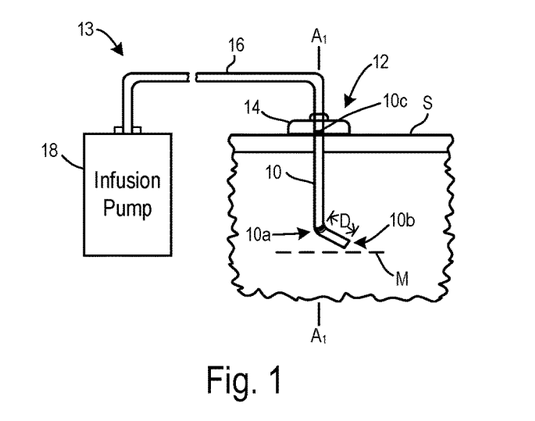
FIG. 1 is a schematic view of a fluid delivery system having a flexible tubing.

In certain examples, the flexible tubing forms a cannula configured to be inserted into or partially into a patient, such as, through the patient's skin. The flexible tubing cannula may be included in an insertion set, an infusion set, a sensor device, an infusion pump or other fluid delivery system, or other medical device or system, or the like. In certain examples, the flexible tubing may be connected to or included in an infusion set that includes a base or pad configured to adhere to the skin S of a patient, as shown in FIG. 1. In the example in FIG. 1, the flexible tubing is included in a fluid deliver system that includes an infusion pump that is configured to deliver fluid from a reservoir, to a patient, through the flexible tubing.

Also as described herein, a flexible tubing according to certain examples described herein may be configured to receive an insertion needle for assisting with insertion of the flexible tubing cannula into or through a patient's skin, a septum or another structure, and to allow withdrawal of the insertion needle from the flexible tubing, once the cannula is inserted. In other examples, the flexible tubing is configured to fit inside of a hollow needle, for insertion into a patient, septum or other structure. The needle can provide sufficient rigidity and a pointed or sharp end, for assisting with inserting the flexible tubing through the patient's skin. In particular examples, the needle is withdrawn, after insertion of the flexible tubing. In certain examples, the flexible tubing may be connected to or included in an infusion set that includes a base or pad configured to adhere to the skin S of a patient, as shown in FIG. 1. In other examples, the flexible tubing may be connected to or included in other types of infusion sets or other medical devices or systems.

A flexible tubing for a medical device or system described herein may have an axial length dimension, a generally circular cross-section shape taken perpendicular to the axial length dimension, and a central passage through which fluid may flow. In other examples, the tubing may have a cross-section shape that is not a circle, such as, but not limited to an oval, another curved shape, a polygon or a shape having a combination of curved and straight edges. The cross-section shape of the central passage may have a circular or another shape, and may correspond to (be the same shape as) the outer cross-section shape of the tubing. In other examples, the cross-section shape of the central passage may be a different shape relative to the outer cross-section shape of the tubing.

The material of the flexible tubing is compatible with fluids intended to be conveyed through the tubing, and with other materials to which the tubing may come into contact or be connected, in the intended environment of use. In certain examples, the flexible tubing is made of a material that is biologically compatible, for use in contexts in which the flexible tubing is in contact or connected with a biological entity (such as a human patient or another biological entity), or is implanted fully or partially in the patient (or other biological entity). In certain examples, the flexible tubing is treated in one or more processes for enhancing biologically compatible such as, but not limited to cleaning, sterilizing, coating with Heparin, or the like.

In certain examples the tubing is made of a material that is suitable for medical uses, including but not limited to materials compatible with, and suitable for, implanting or partially implanting into a patient or other biological entity. Alternatively or in addition, the tubing material is selected to be compatible with and suitable for conveying one or more desired or predefined fluids (such as, but not limited to insulin, cancer or AIDs treatment drugs, or other medications, drugs or therapy fluids). Such materials may include, but are not limited to a polyether block amide (PEBA) of thermoplastic elastomer (TPE) such as PEBAX™, a polytetrafluoroethylene (PTFE), an ethylene tetrafluoroethylene (ETFE), a thermoplastic polyurethane (TPU) such as PELLETHAN™, a fluorinated ethylene propylene (FEP) or other fluoropolymer, an ethylene vinyl acetate (EVA), a silicon material or the like. However, for other contexts and applications of use, the tubing may be made of other materials suitable and compatible with those contexts and applications. The tubing may be made by any suitable manufacturing process including, but not limited to extrusion, molding, machining, shrinking over a mandrel, or the like.

An example of a flexible tubing 10 is shown in FIG. 1, as connected to or included in an infusion set 12, and as connected to or included in a fluid delivery system 13 that includes the infusion set 12. The infusion set 12 includes a base or pad 14 that is configured to adhere to the outer surface of a patient's skin S. In particular examples, the base or pad 14 may include a surface that faces the skin S, on which an adhesive is provided, to adhere the base or pad 14 to the skin S. The flexible tubing 10 extends from a base 14 of the infusion set 12, in a direction to extend through a patient's skin, when the base 14 is adhered to the patient's skin. A further tubing 16 extends from the infusion set 12 to an infusion pump device 18. In some examples, the tubing 16 may be part of the flexible tubing 10. In other examples, the tubing 16 is a separate fluid flow tubing (e.g., a separate length of flexible tubing of any suitable length) that connects the base 14 in fluid flow communication with the infusion pump device 18.

In the example of FIG. 1, the flexible tubing 10 has a hollow tubular body having a length dimension, a section 10a along a portion of the length dimension, a first end 10b and a second end 10c. The section 10a of the tubing 10 is located between and spaced apart from the first end 10b and the second end 10c, and is shown in FIG. 1 as forming a bend along the length dimension of the flexible tubing 10. The first end 10b of the flexible tubing 10 is arranged to be inserted and located subcutaneously (below the patient's skin S) when the base 14 is adhered to the patient's skin, during use. The second end 10c of the flexible tubing 10 is arranged to be located within the base 14 (or external to the skin S), when the base 14 is adhered to the patient's skin, during use. The length dimension of the flexible tubing 10 extends at least partially along an axis $A_1$ dimension. In particular examples, the flexible tubing 10 has a linear section along the axis $A_1$, at a location at which the tubing 10 extends through the skin S, when the tubing 10 is in an inserted state as shown in FIG. 1.

In FIG. 1, the bend at the section 10a of the flexible tubing 10 has occurred, due to a compression force provided on the flexible tubing 10, when or after the flexible tubing was inserted into the patient. The compression force may be due to the flexible tubing 10 coming into contact with muscle or other tissue of higher density M, than tissue directly under the skin S.

In particular examples, the section 10a of the flexible tubing 10 is configured with a greater or enhanced flexibility relative to other sections of the flexible tubing 10. The section 10a of enhanced flexibility is located along the length dimension, at a distance D from the first end 10b.

As described herein, the section 10a of enhanced flexibility exhibits a greater degree of bending flexibility than other sections of the flexible tubing 10. In particular examples, the section 10a of enhanced flexibility provides a sufficiently greater degree of flexibility (relative to one or more other sections of the flexible tubing) such that, upon receiving a compression or bending force, the flexible tubing will tend to bend only (or primarily) at the section of enhanced flexibility.

Also in particular examples, the section of enhanced flexibility is provided at a selected location along the length dimension of the flexible tubing, so as to be located a selected distance D (or within a range of distances D1 to D2 discussed below) from the first (or distal) end of the flexible tubing. In certain examples, the distance D (or range of distances D1 to D2) is selected such that the enhanced section of flexibility is located at a desired position below the skin S (or a desired distance from the end 10a of the tubing 10), when the flexible tubing is in an installed or inserted state, and extended through the patient's skin.

Examples of flexible tubings 20, 30, 40, 50, 60, 70, 80, 90, 100, 110, 120, 130, 140, 150 and 170, each having one or more sections of enhanced flexibility are shown in FIGS. 2-15 and 17. Each of the flexible tubings 20, 30, 40, 50, 60, 70, 80, 90, 100, 110, 120, 130, 140, 150 and 170 has a circular cross-section shape defining an axial dimension. Each of the flexible tubings in FIGS. 2-17 has a length from a first (or distal) end shown in the drawings, to a second end (not shown in the drawings), where the length extends along the axial dimension (linearly, when the tubing is not bent, or non-linearly when the tubing is bent). The length of the tubing from the first end to the second end may be any suitable length, for example, selected in accordance with the context of use. In some contexts, the length of the tubing may be relatively long, while in other contexts, the length of the tubing may be relatively short. In certain contexts, the tubing length is suitable for use as a cannula in a medical device, system or process as described herein.

For example, the length of the tubing may be in the range of about 4.0 mm to about 8.0 mm. In other examples, the length of the tubing may be greater than 8.0 mm, or may be shorter than 4.0 mm. In particular examples, the length of the tubing may be a first length for use with patients having a skin thickness below a selected threshold, or a second length for use with patients having a skin thickness at or above the selected threshold. (Additionally or alternatively, as skin thickness can be related to body weight, the first length may correspond to tubing used for patients having a body weight below a specified threshold, while the second length may correspond to tubing used for patients having a body weight at or above the specified threshold.) In some examples, the first length is about 6 mm, the second length is about 9 mm, and the threshold skin thickness is 4 mm. Other examples may include other suitable dimensions for larger or smaller patients or define other specified skin thickness thresholds or body weight thresholds.

Each of the flexible tubings in FIGS. 1-17 may be hollow from the first end to the second end, and may have an outside diameter and an inside diameter. In particular examples, the outside diameter of the tubing body is sufficiently small to be appropriate for use as a cannula configured to be inserted through a patient's skin, and to remain in the inserted state for a period of time (e.g. during a treatment). In certain examples, the outside diameter is no greater than about 0.9 mm (and, preferably, no greater than about 0.7 mm). In particular examples, the inside diameter of the tubing body is suitable for conveying fluid to or from the patient. In certain examples, the outside diameter may be within the range of about 0.3 mm to about 0.7 mm, and the inside diameter may be within the range of about 0.2 mm to about 0.6 mm. In other examples, the tubing may have another suitable outside diameter or inside diameter (or both).

For purposes of explanation, each of the flexible tubings in FIGS. 1-4 is shown in an installed or inserted state, in which the flexible tubing extends through a skin S of a patient. In other examples, the skin S may represent another membrane, septum or other material through which the tubing extends, during use. The relative dimensions of the tubing structures shown in the drawings of FIGS. 1-17 may differ in different embodiments, and the dimensions shown in the drawings are for purposes of assisting with explanation and not intended to limit the invention. For example, tubing structures having features as described herein, but with any suitable relative dimensions for tubing length, tubing section length, inside diameter, outside diameter, or tubing wall thickness may be employed. In some examples, the length and diameter of the tubing is selected or determined, based on the context of use, or the dimensions of the medical device to which it is connected or of which it is a component.

In each of the drawings of FIGS. 1-15 and 17, the flexible tubing has a section of enhanced flexibility located along its length dimension, between the first and second ends. In other examples, a flexible tubing may include more than one (a plurality of) sections of enhanced flexibility along its length. Each section of enhanced flexibility may be formed as described herein, or in any suitable manner, to provide a higher degree of flexibility relative to other sections of the length of the flexible tubing. In certain examples as described herein, each section of enhanced flexibility may include one or more (or a plurality of) folds or convolutions in the tubing wall. In some examples, a plurality of folds or convolutions provides an accordion-like wall structure that exhibits a relatively high degree of flexibility (compared to other sections of the tubing). In other examples as described herein, each section of enhanced flexibility may include a thinner wall thickness (compared to other sections of the tubing), or other features or combinations of features for enhancing flexibility.

Figure 2:
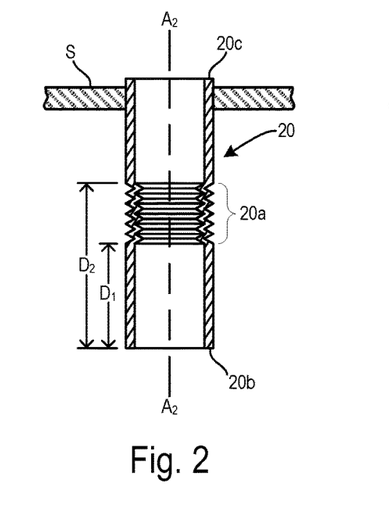
FIG. 2 is a cross-section view of an example of a flexible tubing.

In the example in FIG. 2, the flexible tubing 20 has a section 20a of enhanced flexibility located along a portion of the length of the tubing, between a first end 20b and a second end 20c. The section 20a of enhanced flexibility is spaced from the first end 20b of the flexible tubing 20. In FIG. 2, the section 20a has one end that is spaced a distance $D_1$ from the first end 20b of the flexible tubing. The section 20a has a second end that is spaced a distance $D_2$ from the first end 20b of the flexible tubing. The section 20a of enhanced flexibility extends continuously from $D_1$ to $D_2$, and may have any suitable length for example, but not limited to a length in the range of about 1.0 mm to about 2.0 mm.

Figure 3:
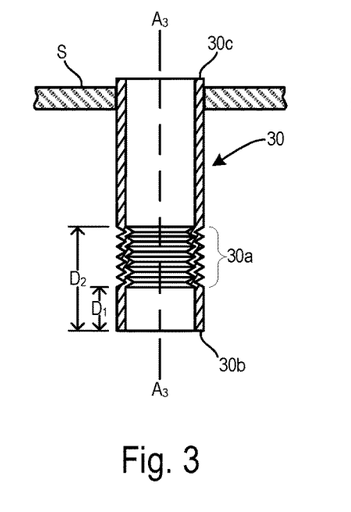
FIG. 3 is a cross-section view of another example of a flexible tubing.

The flexible tubing 30 in the example of FIG. 3 is similar to the flexible tubing 20 of FIG. 2, and has a section 30a of enhanced flexibility, a first end 30b, and a second end 30c, where the section 30a of enhanced flexibility located extends between distances $D_1$ and $D_2$ from the first end 20b of the flexible tubing. However, the distance $D_1$ in FIG. 3 is shorter than the distance $D_1$ in FIG. 2. Accordingly, in FIG. 3, the region 30a of enhanced flexibility is located closer to the first end 30b, than the region 20a of enhanced flexibility (relative to the first end 20b) in FIG. 2. Therefore, when a sufficient compression or bending force is applied, the flexible tubing 30 will tend to bend in the region 30a (located between distances $D_1$ and $D_2$ from the first end of the flexible tubing), which is closer to the first end 30b (as compared to the location of the region 20a relative to the first end 20b of the flexible tubing 20).

In particular examples, the distance $D_1$ (or the location at which the section of enhanced flexibility begins, relative to the first end of the flexible tubing) is selected or configured, based on the length of the tubing (e.g., the length of the tubing between first and second ends, or the length of the tubing that will extend below the skin S, when the tubing is inserted in the patient, or in use). Alternatively or in addition, the distance $D_1$ (or the location at which the section of enhanced flexibility begins, relative to the first end of the flexible tubing) is selected or configured, based on the thickness of the skin S of the patient, or based on the body weight of the patient.

For example, a flexible tubing having the smaller length (or first length) discussed above (e.g., for use with patients having a skin thickness or a body weight below a selected threshold), may have a section of enhanced flexibility that is at (or begins at) a first distance $D_1$ relative to the first end of the flexible tubing, where the first distance $D_1$ has a first value (such as, but not limited to 4.0 mm) or a value within a first range (such as, but not limited to greater than 3.0 mm to 5.0 mm). On the other hand, a flexible tubing having the larger length (or second length) discussed above (e.g., for use with patients having a skin thickness or a body weight at or above the selected threshold), may have a section of enhanced flexibility that is at (or begins at) a first distance $D_1$ relative to the first end of the flexible tubing, where the first distance $D_1$ has a second value (such as, but not limited to 2.0 mm) or a value within a first range (such as, but not limited to 1.0 mm to 2.9 mm).

In that regard, a flexible tubing having the second (or longer) length dimension is configured such that the section of enhanced flexibility is located closer to the first end of the tubing, as compared to a flexible tubing have a first (or shorter) length dimension. Therefore, a flexible tubing having the second length may be employed with a patient having a skin thickness or body weight at or above the selected threshold (e.g., a thicker skin or greater body weight relative to patients that are below the skin thickness or body weight threshold), such that the section of enhanced flexibility is more likely to be located in subcutaneous fatty tissue below the skin, after the tubing is inserted or during use.

On the other hand, a flexible tubing having the first (or smaller) length dimension is configured such that the section of enhanced flexibility is located further from the first end of the tubing, as compared to a flexible tubing have a second (or larger) length dimension. Therefore, a flexible tubing having the first length may be employed with a patient having a skin thickness or body weight below the selected threshold (e.g., a thinner skin or lower body weight relative to patients that are at or above the skin thickness or body weight threshold), such that the section of enhanced flexibility may be likely located in subcutaneous fatty tissue below the skin, but is able to bend at a location that is relatively close to the skin S.

In the examples in FIGS. 2 and 3, the section 20a or 30a of enhanced flexibility includes one or more (or a plurality of) folds or convolutions in the tubing wall, that provide an accordion-like wall structure having a relatively high degree of flexibility (compared to other sections of the tubing). In particular examples, the folds or convolutions of the accordion-like wall structure unfold and flatten out (or partially unfold and partially flatten out) on one side of the flexible tubing, when the flexible tubing is bent at the section of enhanced flexibility.

In particular examples, the one or more (or plurality of) folds or convolutions extend around the entire circumference of the tubing wall. In such examples, a plurality of folds or convolutions may define annular grooves between adjacent folds or convolutions. In other examples, the one or more folds or convolutions may be configured to define a spiral or helical groove.

Figure 4:
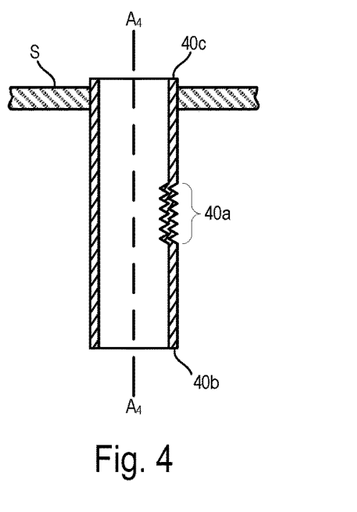
FIG. 4 is a cross-section view of another example of a flexible tubing.

In other examples, the one or more (or plurality of) folds or convolutions are located on a portion (or arc) of the circumference, but not the entire circumference, such as shown in FIG. 4. In FIG. 4, the tubing 40 has a section 40a of enhanced flexibility, a first end 40b, and a second end 40b. In the section 40a in FIG. 4, the tubing wall on one side of the axis $A_4$ (i.e., the right side in the orientation of FIG. 4) has folds or convolutions, while the tubing wall on the opposite side of the axis $A_4$ has a smooth surface or no folds or convolutions. The section 40a of enhanced flexibility in the example in FIG. 4, is shown at a distance from the first end 40b corresponding to the distance $D_1$ in FIG. 2. In other examples, the section 40a of enhanced flexibility may be located at any other suitable distance $D_1$, including but not limited to the distance $D_1$ shown in FIG. 3.

Figure 5:
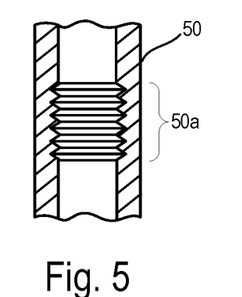
FIG. 5 is a cross-section view of a portion of another example of a flexible tubing.
Figure 6:
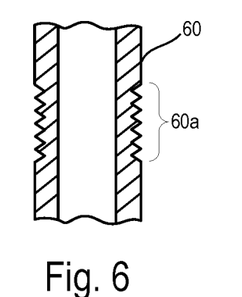
FIG. 6 is a cross-section view of a portion of another example of a flexible tubing.

In the examples of FIGS. 2, 3 and 4, the folds or convolutions are provided on both the inner and the outer surfaces of the section 20c, 30c or 40c or the flexible tubing 20, 30 or 40. In other examples, as shown in FIG. 5, a tubing 50 (e.g., corresponding to any of the tubings 20, 30 or 40 or other suitable tubing) has one or more (or a plurality of) folds or convolutions are provided on the inner surface of a section 50a of enhanced flexibility (e.g. corresponding to sections 20a, 30a or 40a), but not on the outer surface, such that the outer surface of the section of enhanced flexibility is smooth. In yet other examples, as shown in FIG. 6, a tubing 60 (e.g. corresponding to any of the tubings 20, 30 or 40 or other suitable tubing) has one or more (or a plurality of) folds or convolutions are provided on the outer surface of a section 60a of enhanced flexibility (e.g. corresponding to sections 20a, 30a or 40a), but not on the inner surface, such that the inner surface of the section of enhanced flexibility is smooth. A smooth inner surface in the section of enhanced flexibility can improve fluid flow in certain contexts.

Figure 7:
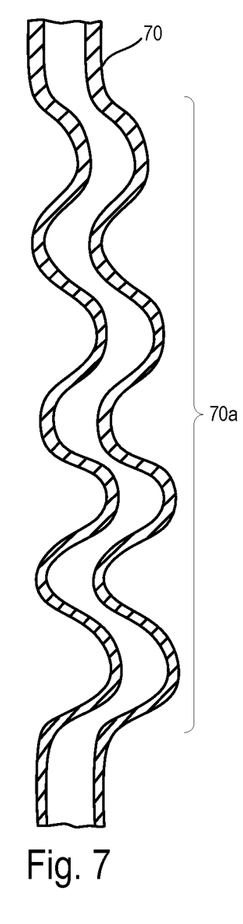
FIG. 7 is a cross-section view of a portion of another example of a flexible tubing.

In any of the examples described with regard to FIGS. 2-6, the section of enhanced flexibility 20a, 30a, 40a, 50a, or 60a may have a plurality of folds or convolutions provided in any suitable pitch (number of folds or convolutions per unit of length). In some examples as shown in FIG. 7, a tubing 70 (e.g. corresponding to any of the tubings 20, 30, 40, 50 or 60, or other suitable tubing) may have a section of enhanced flexibility 70a (e.g. having a configuration corresponding to any of sections 20a, 30a, 40a, 50a, or 60a), but where the plurality of folds or convolutions are at a smaller pitch than that shown in FIGS. 2-6, for example, providing a wavy shape. In other examples, a tubing may have a plurality of folds or convolutions in configurations corresponding to any of the tubings 20, 30, 40, 50 or 60, but with a greater pitch than that shown in FIGS. 2-6. In certain examples, the pitch is within a range of 1 to 10 folds or convolutions per millimeter. Other examples may have other suitable pitches. In any of the examples described with regard to FIGS. 2-7, when the tubing is in an unbent state, the one or more folds or convolutions in the section of enhanced flexibility 20a, 30a, 40a, 50a, 60a, or 70a may have any suitable shape, including shapes having sharp or angled apexes as shown in FIGS. 2-6, or other shapes having curved or rounded apexes, or combinations thereof.

Figure 8:
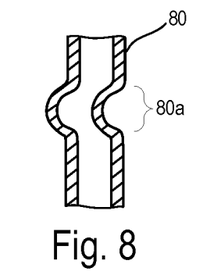
FIG. 8 is a cross-section view of a portion of another example of a flexible tubing.
Figure 9:
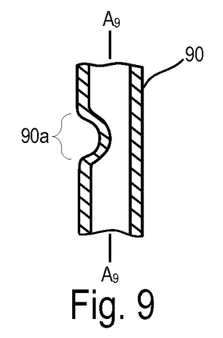
FIG. 9 is a cross-section view of a portion of another example of a flexible tubing.
Figure 10:
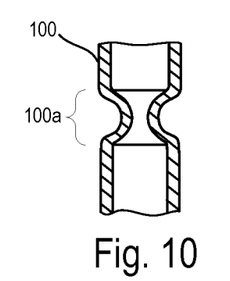
FIG. 10 is a cross-section view of a portion of another example of a flexible tubing.
Figure 11:
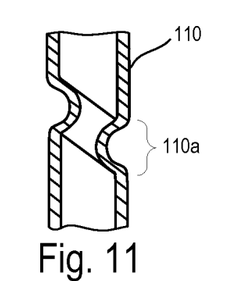
FIG. 11 is a cross-section view of a portion of another example of a flexible tubing.

In certain examples as shown in FIGS. 8, 9, 10, and 11 a tubing 80, 90, 100, 110 (e.g. corresponding to any of the tubings 20, 30, 40, 50, 60 or 70, or other suitable tubing) may have a section of enhanced flexibility 80a, 90a, 100a, 110a (e.g. having a configuration corresponding to any of sections 20a, 30a, 40a, 50a, 60a, or 70a), but with a single fold or convolution. In the example of FIG. 8, the single fold or convolution bows or protrudes in one direction (to the left in the orientation of FIG. 8) and is formed around the circumference of the tubing 80, defining a serpentine fluid flow path within the tubing 80. In the example of FIG. 9, the single fold or convolution extends inward and is formed around a portion of, but not the entire circumference of the tubing 90, such that the wall of the tubing on one side of the longitudinal axis $A_9$ of the tubing (the left side of the tubing in the orientation of FIG. 9) is bowed inward, while the tubing wall on the other side of the axis $A_9$ (the right side of the tubing in the orientation of FIG. 9) is not bowed (is smooth). In the example of FIG. 10, the single fold or convolution extends inward toward the longitudinal axis $a_{10}$ of the tubing 100 and is formed around the entire circumference of the tubing 100. In the example of FIG. 11, the single fold or convolution extends in a spiral or helical shape along the section 110a of the tubing 100.

In certain examples as shown in FIGS. 12-15, a tubing 120, 130, 140 or 150 (e.g. corresponding to any of the tubings 20, 30, 40, 50, 60, 70, 80, 90, 100 or 110, or other suitable tubing) may have a section of enhanced flexibility 120a, 130a, 140a or 150a having one or more thinner wall portions (relative to other portions of the wall of the tubing 120, 130, 140, or 150), instead of (or in addition to) one or more folds or convolutions.

Figure 12:
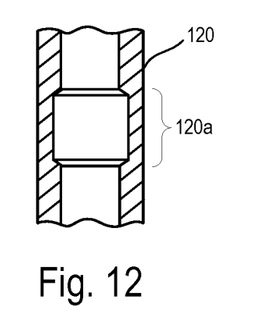
FIG. 12 is a cross-section view of a portion of another example of a flexible tubing.
Figure 13:
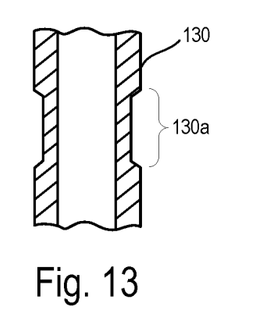
FIG. 13 is a cross-section view of a portion of another example of a flexible tubing.
Figure 14:
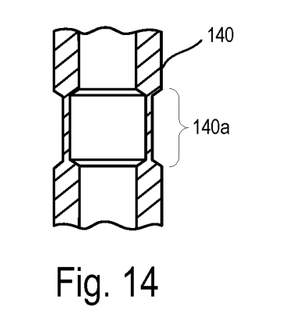
FIG. 14 is a cross-section view of a portion of another example of a flexible tubing.
Figure 15:
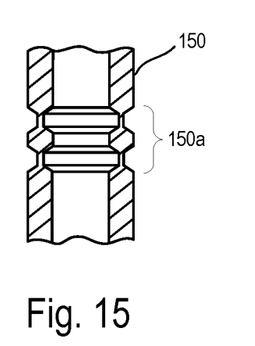
FIG. 15 is a cross-section view of a portion of another example of a flexible tubing.

In the example of FIG. 12, the tubing 120 has a single thinner wall portion, where the inner surface of the tubing wall is recessed, but the outer surface of the tubing is smooth and not recessed in the section 120a. In the example of FIG. 13, the tubing 130 has a single thinner wall portion, where the outer surface of the tubing wall is recessed, but the inner surface of the tubing is smooth and not recessed in the section 130a. In the example of FIG. 14, the tubing 140 has a single thinner wall portion, where both the inner surface and the outer surface of the tubing wall is recessed in the section 140a. The example of FIG. 15 is similar to the example of FIG. 14, but where the section 150a of enhanced flexibility has two thinner wall portions. In other examples, the section 150a of enhanced flexibility may have more than two thinner wall portions, or may include one or more thinner wall portions having a configuration as shown in FIGS. 12-14.

Figure 16:
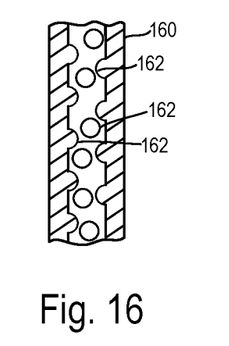
FIG. 16 is a cross-section view of a portion of another example of a flexible tubing.
Figure 17:
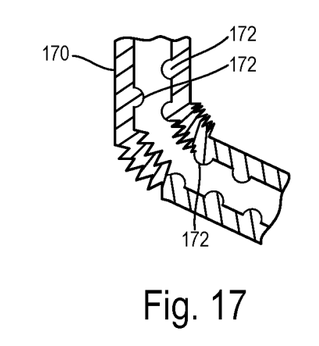
FIG. 17 is a cross-section view of a portion of another example of a flexible tubing.

In any of the examples described with regard to FIGS. 2-15, the tubing may include one or more bumps, bubbles or protrusions on the inner wall surface. An example of a tubing 160 having a plurality of bumps, bubbles or protrusions (some of them labeled with reference number 162) on the inner wall surface is shown in FIG. 16. Each bump, bubble or protrusion extends inward from the inner side wall, a distance toward the longitudinal axis of the tubing, but is sufficiently small and shaped so as to minimize obstruction of fluid flow in the fluid flow path through the tubing. In certain examples as shown in FIG. 17, a tubing 170 may include one or more bumps, bubbles or protrusions arranged adjacent or along a section 170a of enhanced flexibility as described herein, to help maintain a fluid flow path within the hollow interior of the tubing, along a bend in the section 170a. In certain examples, the tubing 170 may include one or more bumps, bubbles or protrusions (some of them labeled with reference number 172) on other portions of the length of the tubing, for inhibiting other sections of the tubing walls from collapsing, buckling or compressing enough to close the fluid flow path at a bent portion. In particular examples, a plurality of protrusions are located at regular intervals or spacing along the length of the tubing, or around a circumference of the inner surface of the tubing, or both. In other examples, a plurality of protrusions are located at irregular intervals or spacing along the length of the tubing, or around a circumference of the inner surface of the tubing, or both.

In any of the examples described with regard to FIGS. 2-17, the tubing may have more than one (a plurality of) sections of enhanced flexibility, each having a configuration as described in those drawings, or having other suitable configurations. In certain examples, a tubing may have a plurality of sections of enhanced flexibility that include a combination of configurations as described in those drawings, or other suitable configurations.

While various exemplary embodiments have been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

We claim:

1. A flexible tubing for a cannula of an infusion device having a base configured to secure to a patient's skin, the flexible tubing extending from the base and comprising a hollow tubing body having a length dimension extending from a first end to a second end and no more than one fluid outlet opening, the fluid outlet opening located at the second end of the tubing body, the tubing body having at least one section of enhanced flexibility located between the first and the second end, the at least one section of enhanced flexibility has a greater flexibility than one or more other sections of the tubing body, wherein the tubing body has a tubing wall having an inner surface and an outer surface, wherein a plurality of bumps, bubbles or protrusions are provided on the inner surface of the tubing wall separate from each section of enhanced flexibility, and protrude inward from the inner surface, wherein each section of enhanced flexibility defines an accordion-like structure in the tubing wall configured to at least partially unfold on one side of the tubing body when the tubing body is bent at the section of enhanced flexibility, wherein the tubing wall is uniform in material between the inner and the outer surface, and wherein the at least one section of enhanced flexibility is provided on the inner surface of the tubing wall, but not on the outer surface of the tubing wall.

2. A flexible tubing as recited in claim 1, wherein the at least one section of enhanced flexibility comprises one or more folds or convolutions in the tubing wall, wherein the folds or convolutions define the accordion-like structure in the tubing wall.

3. A flexible tubing as recited in claim 2, wherein the tubing body defines a circumference and wherein each of the one or more folds or convolutions extend around the entire circumference of the tubing body.

4. A flexible tubing as recited in claim 2, wherein the tubing body defines a circumference and wherein the one or more folds or convolutions extend around part of, but not the entire circumference of the tubing body.

5. A flexible tubing as recited in claim 2, wherein the one or more folds or convolutions form a spiral or helical shape on the tubing wall.

6. A flexible tubing as recited in claim 2, wherein the plurality of folds or convolutions are provided at a pitch within the range of 0.125 mm and 1.0 mm.

7. A flexible tubing as recited in claim 1, wherein the at least one section of enhanced flexibility is spaced from the first end of the tubing body by a distance D, where D is within a range of 3.0 mm to 5.0 mm.

8. A flexible tubing as recited in claim 7, wherein the length dimension of the tubing body is no more than about 6.0 mm.

9. A flexible tubing as recited in claim 1, wherein the at least one section of enhanced flexibility is located at a distance D from the first end of the tubing body, where D is within a range of 1.0 mm to 2.9 mm.

10. A flexible tubing as recited in claim 9, wherein the length dimension of the tubing body is greater than 6.0 mm, but no more than about 9.0 mm.

11. A flexible tubing as recited in claim 1, wherein the at least one section of enhanced flexibility comprises no more than one fold or convolution in the tubing wall.

12. A flexible tubing as recited in claim 11, wherein the fold or convolution extends around an entire circumference of the tubing body.

13. A flexible tubing as recited in claim 11, wherein the fold or convolution extends around part of, but not an entire circumference of the tubing body.

14. A flexible tubing as recited in claim 11, wherein the fold or convolution forms a spiral or helical shape on the tubing wall.

15. A flexible tubing as recited in claim 1, wherein the hollow tubing body has an outer diameter of no more than 0.9 mm.

16. A flexible tubing as recited in claim 1, wherein the at least one section of enhanced flexibility comprises no more than one section of enhanced flexibility.

17. A flexible tubing as recited in claim 1, wherein each section of enhanced flexibility is free of the plurality of bumps, bubbles or protrusions.

18. A method of making a flexible tubing for a cannula of an infusion device having a base configured to secure to a patient's skin, the method comprising: forming by molding a hollow tubing body having a length dimension extending from a first end to a second end and no more than one fluid outlet opening, the fluid outlet opening located at the second end of the tubing body, the tubing body having a tubing wall with an inner surface and an outer surface; extending the tubular body from the base; providing the tubing body with at least one section of enhanced flexibility located between the first and the second end, the at least one section of enhanced flexibility having a greater flexibility than one or more other sections of the tubing body; and providing a plurality of bumps, bubbles or protrusions on the inner surface of the tubing wall separate from each section of enhanced flexibility, and protruding inward from the inner surface; wherein providing the tubing body with at least one section of enhanced flexibility comprises providing one or more folds or convolutions in a wall of the tubing, wherein the folds or convolutions define an accordion-like structure in the tubing wall configured to at least partially unfold on one side of the tubing body when the tubing body is bent at the section of enhanced flexibility, wherein the tubing wall is uniform in material between the inner and the outer surface, and wherein the at least one section of enhanced flexibility comprising the one or more folds or convolutions is provided on the inner surface of the tubing wall, but not on the outer surface of the tubing wall.

19. A method as recited in claim 18, wherein the at least one section of enhanced flexibility is spaced from the first end of the tubing body by a distance D, where D is within a range of 1.0 mm to 2.9 mm and the length dimension of the tubing body is no more than about 6.0 mm, or where D is within a range of 3.0 mm to 5.0 mm and the length dimension of the tubing body is greater than 6 mm and no more than about 9.0 mm.

20. A flexible tubing for a cannula of an infusion device having a base configured to secure to a patient's skin, the flexible tubing extending from the base and comprising a hollow tubing body having a length dimension extending from a first end to a second end, the tubing body having no more than one section of enhanced flexibility located between the first and the second end, the section of enhanced flexibility has a greater flexibility than one or more other sections of the tubing body, wherein the tubing body has a tubing wall having an inner surface and an outer surface, wherein a plurality of bumps, bubbles or protrusions are provided on the inner surface of the tubing wall separate from the section of enhanced flexibility, and protrude inward from the inner surface, wherein the section of enhanced flexibility is free of the plurality of bumps, bubbles or protrusions, wherein the section of enhanced flexibility defines an accordion-like structure in the tubing wall configured to at least partially unfold on one side of the tubing body when the tubing body is bent at the section of enhanced flexibility, wherein the tubing wall is uniform in material between the inner and the outer surface, and wherein the section of enhanced flexibility is provided on the inner surface of the tubing wall, but not on the outer surface of the tubing wall.

* * * * *